United States Patent
Suzuki et al.

(10) Patent No.: US 6,569,137 B2
(45) Date of Patent: May 27, 2003

(54) ABSORBENT INCONTINENCE PADS

(76) Inventors: Migaku Suzuki, c/o Japan Absorbent Technology Institute, 2-26-5 Nihonbashi Hamacho, Chuo-ku, Toyko (JP); Kenichi Uchimoto, c/o Toyoeizai Co., Ltd., 45-2 Handa otsu, Kaneda-cho, Kawanoe-shi, Aichi-ken (JP); Kenji Nakaoka, c/o Toyoeizai Co., Ltd., 45-2 Handa otsu, Kaneda-cho, Kawance-shi, Aichi-ken (JP)

( * ) Notice: Subject to any disclaimer, the term of this patent is extended or adjusted under 35 U.S.C. 154(b) by 188 days.

(21) Appl. No.: 09/758,225

(22) Filed: Jan. 12, 2001

(65) Prior Publication Data
US 2001/0014797 A1 Aug. 16, 2001

(30) Foreign Application Priority Data
Jan. 12, 2000  (JP) .......................... 2000-003824

(51) Int. Cl.$^7$ ................................ A61F 13/15
(52) U.S. Cl. .................. 604/385.01; 604/378; 604/381; 604/368
(58) Field of Search ................. 604/378, 381, 604/368, 385.01

(56) References Cited

U.S. PATENT DOCUMENTS

| | | | |
|---|---|---|---|
| 4,840,692 A | 6/1989 | Kamstrup-Larsen | |
| 5,662,634 A | * 9/1997 | Yamamoto et al. | 156/229 |
| 5,728,083 A | * 3/1998 | Cohen et al. | 156/296 |
| 5,938,650 A | 8/1999 | Baer et al. | |
| 5,964,743 A | 10/1999 | Abuto et al. | |

FOREIGN PATENT DOCUMENTS

| | | |
|---|---|---|
| EP | 0875224 | 11/1998 |
| WO | 96/29967 | 10/1996 |
| WO | 98/36720 | 8/1998 |
| WO | 99/47094 | 9/1999 |

* cited by examiner

Primary Examiner—John J. Calvert
Assistant Examiner—Angela J Grayson
(74) Attorney, Agent, or Firm—Hunton & Williams

(57) ABSTRACT

An absorbent incontinence pad is provided with a liquid impervious air permeable back sheet and an absorbent unit partly covered by the back sheet, wherein the absorbent unit has a non-woven fabric substrate, an absorbent zone formed by a plurality of highly absorbent layers extending in the form of bands on the surface of the non-woven fabric substrate and an air permeable zone where no such highly absorbent layer exists, which has sufficiently adequate properties to meet incontinence requirements and provides a comfortable feeling during use.

36 Claims, 5 Drawing Sheets

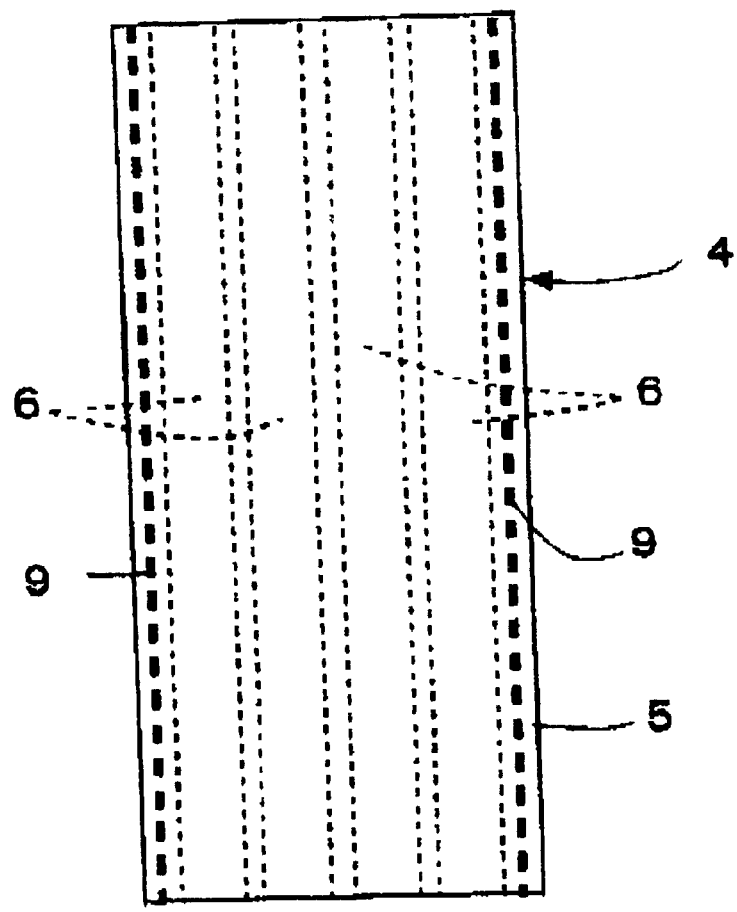
F I G. 3
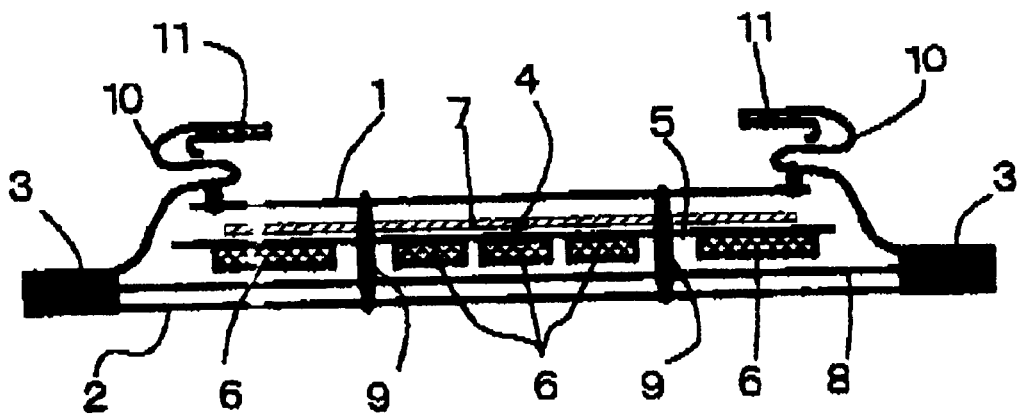
F I G. 4

ABSORBENT INCONTINENCE PADS

BACKGROUND OF THE INVENTION

1. Field

The present invention relates to thin compact absorbent incontinence pads and more particularly to absorbent incontinence pads to be applied onto the crotch region of a user for dealing with his or her light incontinence. The term "incontinence pads" is herein used to collectively refer to absorbent articles for incontinence uses and includes all articles generally called absorbent sheets, absorbent liners or absorbent cards. Also, for the sake of simplicity in designing articles according the amounts of urination, the term "light incontinence" is herein used generally as a term referring to 250 cc or less as the amount of urination, as opposed to the term "serious incontinence," which generally refers to greater amounts of urination.

2. Related Art

In recent years, sanitary goods designed to address adult light incontinence have drawn much market attention, and many companies have actively joined the competition of developing such goods. Symptoms of light incontinence are more often observed with females: the degree of incontinence varies from extremely light (15 cc or less) to medium light (approximately 200 cc), and the age group of those suffering from such symptoms varies widely from the 20's to the 50's. Until now, there have been very few goods designed specifically to deal with adult light incontinence symptoms, and other articles, such as sanitary napkins and panty shields have been used as substitutes.

Articles such as sanitary napkins and panty shields, which were originally designed to deal with menstrual blood, cause many problems when they are used to address urinary incontinence. Articles designed and manufactured to address light urinary incontinence using wood pulp as the absorbent member have also been found to cause many problems.

One problem that articles currently used to treat adult light incontinence have is with leakage and discomfort, typically manifested as a sticky feeling, because they provide insufficient absorbance and performance. One cause of these and other problems is that in baby diapers and adult incontinence diapers one critically important feature is the ability to rapidly absorb large amounts of liquid exudates discharged at one time. This is known as the acquisition effect. In contrast, articles designed for light incontinence symptoms, must be able to efficiently and effectively handle liquid exudates which are usually discharged in small amounts and at more frequent intervals. Adult light incontinence articles which are designed based on baby diapers and adult incontinence diaperstypically use wood pulp fluff as their main component. When used to address adult light incontinence, the wood pulp fluff remains wetted on the surface, causing the skin of the wearer, which is in contact with the absorbent member, to erupt in a rash or become inflamed.

In order to solve such problems, it is preferred to design an adult light incontinence article which takes advantage of the performance of super absorbent polymers (SAP), which are excellent at gelatinizing liquid exudates. It is further preferred that such absorbent member has a high content of SAP, preferably nearly 100% content of SAP.

Another second problem with current absorbent articles is that the absorbent member remains wetted during use. To address this issue, it is critically important to create an absorbent member with an air permeable structure so that it remains breathable during use and does not become uncomfortably stuffy. In order to achieve such a structure, not only must the components such as the topsheet (surface sheet) and backsheet be air permeable, but the absorbent member itself musthave an air permeable structure.

A third problem that must be addressed by an adult light incontinence article is that those who suffer from light incontinence symptoms typically experience such symptoms unpredictably, instantaneously and at times of temporary physical tension or high stress. For example, light incontinence often results from changes in abdominal pressure caused by normal pregnancy, or by sneezing, sudden laughter, or physical exertion such as jumping. In other words, such symptoms are very often observed with those females who live normal and healthy life. It is therefore a very important that an incontinence article can be worn as inconspicuously as possible and has a very thin and compact form so that it additional or spare articles can be carried in a handbag or pocket.

A fourth problem that must be addressed by an incontinence article is that users come in a great variety of shapes and sizes. An absorbent article must have three-dimensional adaptability which can accommodate any difference in shape of the body region of a wearer on which it is applied.

The object of the present invention is to provide an absorbent incontinence pad satisfying all of the above-mentioned requirements.

SUMMARY OF THE INVENTION

According to one aspect of the present invention, there is provided an absorbent incontinence pad comprising:

- an absorbent unit comprising a non-woven fabric substrate, an absorbent zone consisting of a plurality of highly absorbent layer elements extending in the form of bands on the surface of the non-woven fabric substrate, and an air permeable zone abutting the non-woven fabric substrate formed in the area where the highly absorbent layers are not formed;
- a back sheet wrapping the absorbent unit leaving part of a surface of the absorbent unit uncovered; and
- an acquisition layer disposed on the surface of the absorbent unit covering at least part of the uncovered surface thereof.

Furthermore, the absorbent unit may be wrapped with a dispersion layer. In this case, it is preferable that an acquisition layer be disposed on the dispersion layer, covering at least part of the uncovered surface of the absorbent unit.

According to another aspect of the present invention, there is provided an absorbent incontinence pad comprising a topsheet consisting of a liquid pervious and air permeable sheet material and a liquid impervious and air permeable backsheet and an absorbent unit disposed between the topsheet and the backsheet. In this aspect of the invention, the absorbent unit is comprised of a non-woven fabric substrate, an absorbent zone formed by a plurality of highly absorbent layers extending in bands on the surface of the non-woven fabric substrate and an absorbent sheet having an air permeable zone in which no such highly absorbent layers exist.

The topsheet and backsheet can be bonded to each other around their perimeter so that a space is formed between the two sheets, and the absorbent unit can be located within this space.

The absorbent unit can be formed of a first absorbent sheet and a second absorbent sheet being folded on each other. In this structure, the first absorbent sheet may be made with highly absorbent layers in several absorbent zones. The second absorbent sheet may be constructed to have one or more highly absorbent layers in positions corresponding to one or all of the absorbent zones of the first absorbent layer.

In one embodiment, the absorbent unit has two absorbent zones. The first absorbent zone may be located in the central region of the first absorbent sheet, and the second absorbent zone being located in the laterally outboard regions of the first absorbent sheet. In such a configuration, it is preferable for the ratio of the width of the first absorbent zone (Aw) to the width of the second absorbent zone (Bw) (Aw:Bw) to be between 1:0.3 to 2.

It is preferred that the highly absorbent layer be made mostly from a super absorbent polymer. It is also preferred that the highly absorbent layer be divided into a plurality of sections or bands.

In addition, the non-woven fabric substrate of the absorbent sheet may be bonded to other elements of the absorbent incontinence pad in the air permeable zone. For example, the non-woven fabric substrate may be bonded to the topsheet, the backsheet, a dispersion sheet or other layers of absorbent sheets. Such bonding can be done by any number of appropriate means, such as adhesive bonding and heat seal bonding.

In addition, the topsheet, the backsheet, the absorbent unit and their component elements can be made of degradable materials.

One benefit of an absorbent incontinence pad manufactured according to the present invention is that it provides good air permeability through the pad, and provides extremely high absorbency. Such a pad provides very comfortable use, and prevents the humidity and body temperature of the user from rising when worn.

Another benefit of an absorbent incontinence pad manufactured according to the present invention is that the components, such as the top sheet, back sheet, absorbent unit, can be made of degradable material. Such a pad can be disposed of in a toilet without clogging the toilet system. Such a pad can also be disposed of by biodegradation or other types of degradation without causing a severe environmental impact.

BRIEF DESCRIPTION OF THE DRAWINGS

FIG. 3 is a plan view showing an embodiment of an absorbent unit in the absorbent incontinence pad of FIG. 1;

FIG. 4 is a schematic cross-section view showing an absorbent incontinence pad in a second embodiment of the present invention;

DESCRIPTION OF THE PREFERRED EMBODIMENTS

Figure 1:
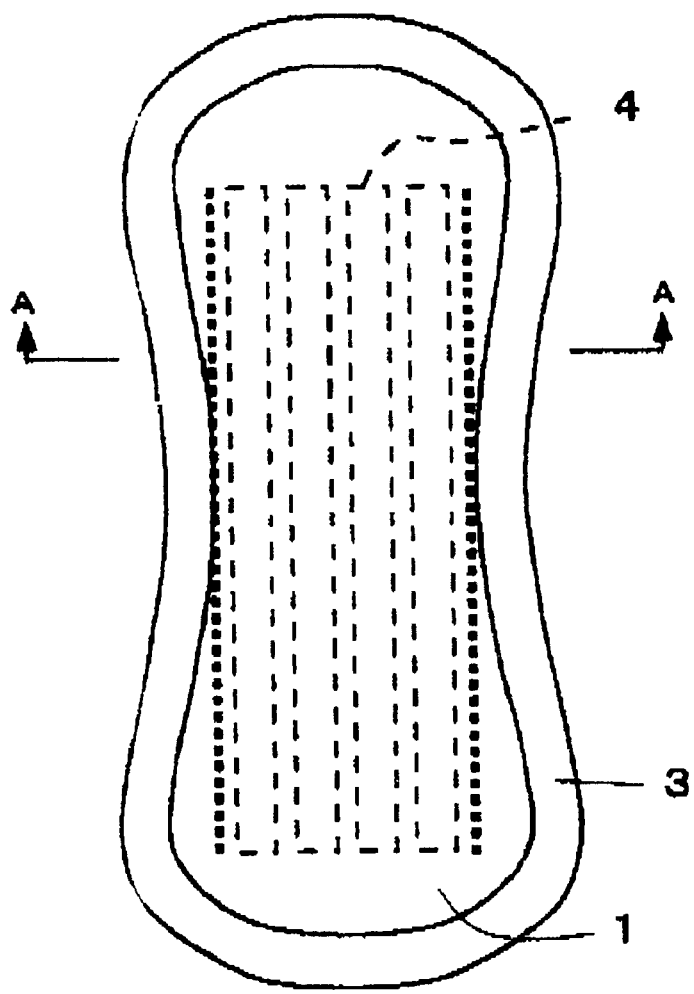
FIG. 1 is a plan view showing an absorbent incontinence pad in a first embodiment of the present invention.

The embodiments of the present invention will be described with reference to the accompanying drawings below:

FIG. 1 shows an embodiment of the present invention in the form of an absorbent incontinence pad designed for a small amount of urine. In FIG. 1, reference number 1 refers to a top sheet and 2 refers to a back sheet. The top sheet 1, is made from a sheet of material, such as porous non-woven fabric or perforated film, which is highly liquid pervious and air permeable. The back sheet 2 is preferably made from film which is porous and through which air or steam can pass, but moisture cannot pass, or a laminate comprised of one or more layers of such a film bonded with one or more layers of non-woven fabric. Alternatively, the back sheet 2 can be comprised of a water resistant laminate of non-woven fabrics of polyethylene or polypropylene, such as a spunbonded-meltblown-spunbonded (S.M.S.) or spunbonded-meltblown-meltblown-spunbonded (S.M.M.S.) fabrics, which are well known in the art. In such a construction, a film, as described before, may not be necessary.

The top sheet 1 and back sheet 2 have at their periphery edges 3 formed by an appropriate means, such as heat sealing or ultrasonic sealing. In addition, an absorbent unit 4 is interposed between the top sheet 1 and the back sheet 2. In one embodiment of the claimed invention, the main absorbent zone in the center of the top sheet 2 may be provided with embossed lines to improve its three-dimensional structure.

Figure 2:
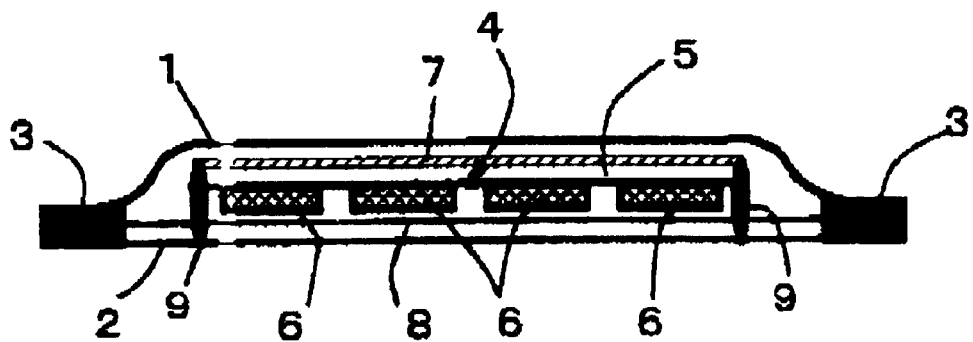
FIG. 2 is a schematic cross-sectional view taken along section line A—A of FIG. 1.

Referring now to FIGS. 2 and 3, in one embodiment of the claimed invention, an absorbent unit 4 may be comprised of an approximately rectangular non-woven fabric substrate 5, which faces the back sheet 2 in this example, located adjacent to a highly absorbent region comprised of a plurality of strands of highly absorbent layers 6, four of which are shown in this example. Between the highly absorbent layer strands 6 there are gaps, which expose the non-woven fabric substrate 5. In this embodiment, the absorbent unit 4 has absorbent zones formed by the highly absorbent layers 6 and zones containing no highly absorbent layers 6, which separate the highly absorbent layers 6 and form an air permeable zone that allows air to flow to the non-woven fabric substrate 5.

The highly absorbent layers 6 are preferable comprised primarily of super absorbent polymer (SAP). In order to obtain as much compactness and absorbency as possible, the highly absorbent layers 6 should have as high a content of SAP as possible, preferably 60% or higher. Such highly absorbent layers 6 can be easily formed on a commercial scale, as described in JPA H10-168230, by applying a dispersion liquid in which particulate super absorbent polymer is deposited on the surface of a non-woven fabric using a device known as a line coater.

In a preferred embodiment of the claimed invention, a dispersion sheet 7 is interposed between the absorbent unit 4 and the top sheet 1. The dispersion sheet 7 is comprised of a liquid pervious non-woven fabric of approximately the same size as the absorbent unit 4. The dispersion sheet 7 traps liquid passing through the top sheet 1 and disperses the liquid in all directions. The dispersion sheet 7, also called an acquisition layer, can be made larger or smaller than the absorbent unit 4, and should preferably be more concentrated in the center zone. Similarly, in a preferred embodiment a piece of tissue 8 may be interposed between the absorbent unit 4 and the back sheet 2. The tissue 8 improves the dispersion of the liquid and improves the dimensional stability of the absorbent incontinence pad. Alternatively, in the case of an absorbent incontinence pad for an extremely small amount of urine, the structure can be made simpler by omitting the dispersion sheet 7 and tissue 8.

Figure 7:
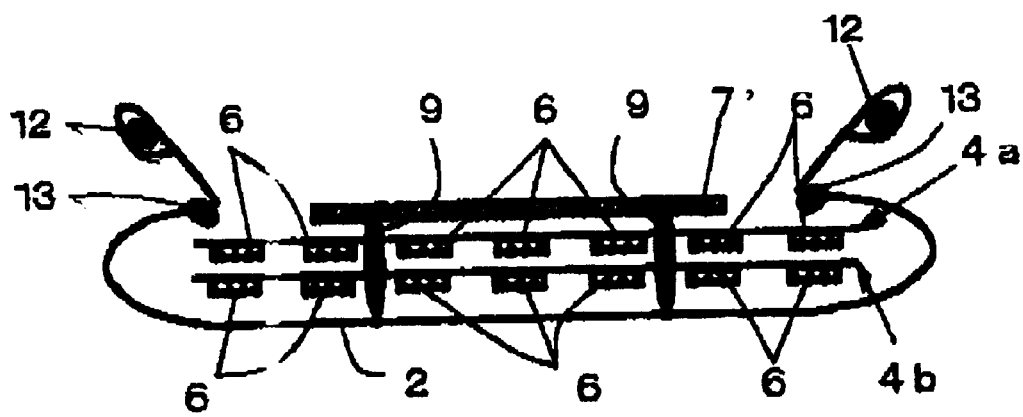
FIG. 7 is a schematic cross-sectional view showing an absorbent incontinence pad in the form of a fourth embodiment of the present invention.
Figure 8:
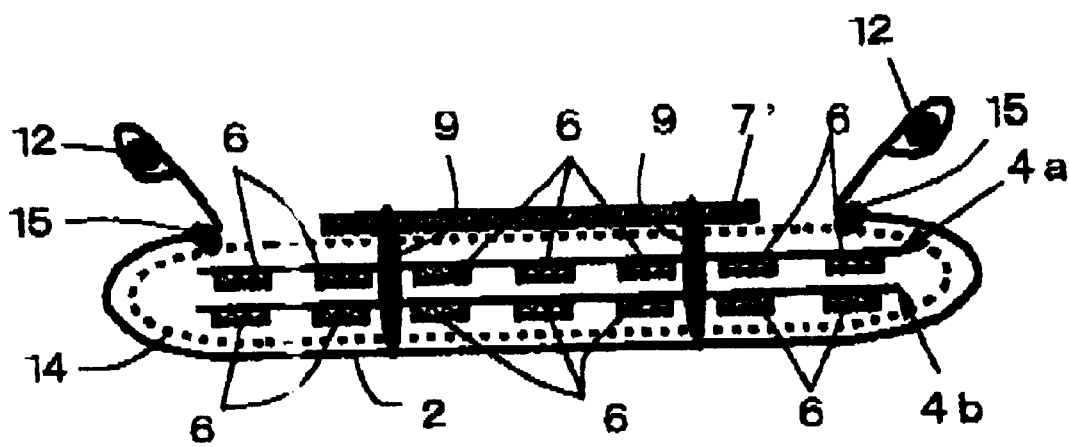
FIG. 8 is a schematic cross-section view showing an absorbent incontinence pad in the form of a fifth embodiment of the present invention.

Although in the previous embodiment the dispersion sheet 7 is between the absorbent unit 4 and the top sheet 1, this configuration may be reversed such that the top sheet 1 is between the acquisition sheet 7 and the absorbent unit 4. Alternatively, as shown in FIGS. 7 and 8, the top sheet may be omitted and replaced by the acquisition layer 7'. Such an embodiment provides an advantage in that the absorbent unit can swell without the upper portion being restrained by the top sheet 1. An acquisition layer for such purposes is preferably a bulky sheet having a weight of approximately 30 g/m$^2$ or compressed member of such material. For example, a bulky perforated film having a embossed thickness as high as 1184$\mu$ (such as that manufactured and sold by Tredegar under the trademark of "X-27373") can be used. Also, a compressed sheet of cellulose sponge of about 100 g/m$^2$ or a bulky non-woven fabric made of hollow bicomponent fiber and having a density of about 50 g/m$^2$ may also be used.

In the present invention, a highly absorbent layer strips 6 are layers containing a super absorbent polymer (SAP). The super absorbent polymers are high polymer materials which can absorb a high volume of water per unit weight of SAP, and generally includes carboxymethyl cellulose, polyacrylic acid and its salts, cross-linked acrylate polymers, starch-acrylic acid graft copolymers, hydrolytes of starch-acrylonitrile graft copolymers, cross-linked polyoxyethylene, cross-linked carboxymethyl cellulose, partially cross-linked water swellable polymers such as polyethylene oxide and polyacrylamide, and isobutylene-maleic acid copolymers. By drying any such polymer, a particulate base polymer can be obtained. After drying, an after treatment is usually further applied to increase the cross-linked density of the surface of the polymer particles, and at the same time, an antiblocking agent is added to prevent the blocking of product particles due to absorption of moisture.

An absorbent incontinence pad structured in accordance with the present invention can, by means of the high absorbancy of super absorbent polymer contained in the highly absorbent layers 6 of the absorbent unit 4, effectively absorb liquid discharged repeatedly and in small amounts, and at the same time maintain the surface of the top sheet 1 in a dry condition. Also, because the absorbent unit 4 has an air permeable zone between the highly absorbent layers 6, exposing the non-woven substrate 5 to air flow, the surface of the top sheet 1 is further assisted in maintaining a dry state. Also, the air permeable zone can also easily bend and deform uniformly, allowing the absorbent article to deform three-dimensionally to match the contours of the wearer's body. Furthermore, the air permeable zone can also serve as a liquid passage to effectively and rapidly distribute discharged liquid to the surfaces of the highly absorbent layers 6.

Since an absorbent light incontinence pad made according to the present invention may be discarded by being flushed down a toilet or discarded in the trash, it is preferred that a biodegradable SAP be used in the article. Biodegradable SAPs are known in the art, such as cross-linked polyolefin, cross-linked carboxymethyl cellulose (as described in the specification of Gelman U.S. Pat. No. 4,650,716), cross-linked alginic acid, crosslinked starch, cross-linked and polyamino acid. Also, by manufacturing the highly absorbent layers 6 with a combination of super absorbent polymer and microfibrillated-fibril-formed cellulose, a structure which may have higher absorbing rate can be obtained.

In the present invention an important component of the absorbent unit 4 is the non-woven fabric substrate 5. The non-woven fabric substrate is may be comprised of what are generally called "non-woven fabrics," such as wet process and dry process spun bonded and spun laced non-woven fabrics. It is preferred that the non-woven fabrics used in the present invention are as bulky as possible, such as spun laced non-woven fabric obtained by entangling carded web in the stream of water and thermally bonded non-woven fabric obtained by thermally bonding carded web. Also, in order to provide a degradable absorbent unit, as combined with the above-mentioned biodegradable SAP, it is preferred that a biodegradable cellulosic non-woven fabric or a non-woven fabric, collapsible in water containing Ca salt of CMC, be selected as the non-woven fabric substrate 5.

It should be understood that the term "degradable absorbent unit" means not merely a degradable absorbent unit but also includes such absorbent units as are collapsible in water, biodegradable, decomposable in compost or decomposable in soil. It should also be understood that, although a degradable absorbent unit 4 has been described herein, an absorbent incontinence pad, as a whole, can be made degradable by appropriately selecting top sheet and back sheet material. For example, an entirely water-collapsible absorbent incontinence pad can be constructed by using an absorbent unit made of water collapsible material, a the top sheet made of non-woven fabric that is collapsible in water, and a back sheet made of material such as partially cross-linked P. V. A. film. Such a water-collapsible pad can be disposed of by flushing it down a toilet.

The following definitions apply to terms that are used in the present invention:

The term "collapsible in water or water-collapsible" means that a component material collapses easily in water in a flush toilet and is capable of dispersing in sufficient fineness so that it does not cause any clogging in a pipe or the like.

The term "biodegradable" means that a component material is decomposed into a safe low molecular weight material by the action of living organisms such as microorganisms, fungi, and enzymes in a natural environment or under artificially controlled conditions such as those for making composts.

The term "degradable in compost" means that a component material is decomposed into a safe low molecular weight material by the action of living organisms such as microorganisms, fungi, and enzymes in compost. For example, when 1 weight part (in dry state) of a degradable absorbent unit is made into 100 weight parts (in wet state) of inoculum of compost and processed at 58 degrees Celsius for 40 days, the dry weight of the degradable absorbent unit after being thus processed is reduced to 0% to 50 of the original dry weight of the degradable absorbent unit.

The term "decomposable in soil" means that a component material is biologically decomposed into a safe low molecular weight material by the action of microorganisms, fungi, or enzymes in soil when it is, for example, buried in soil. For example, when 1 weight part (in dry state) of a degradable absorbent unit is processed by being buried at 300 cm below the ground level of an agricultural field for six months, the dry weight of the degradable absorbent unit after being thus processed is reduced to 0% to 50% of the original dry weight of the degradable absorbent unit.

All of the aforementioned terms are understood to be used interchangeably for the purposes of this invention. Furthermore, and as stated before, all of the terms are included in the definition of the general term: "degradable."

A second embodiment of a regular type absorbent incontinence pad as structured according to the present invention is explained with reference to FIG. 4. In this embodiment, a dispersion sheet 7 is interposed in the space between the top sheet 1 and the back sheet 2. Similarly, a piece of tissue 8 is disposed in the space between an absorbent unit 4 and the back sheet 2. The dispersion sheet 7 and the tissue 8 are located to improve the dispersion of liquid and the dimensional stability of the absorbent incontinence pad as a whole. This structure is similar to the first embodiment as shown in FIGS. 1 through 3, but is different in several respects. One difference is that a fringe member 10 is bonded on the peripheral edge 3 of the back sheet 2, and an elastic member 11 is attached to the inner peripheral edge of the fringe member 10 such that the fringe member 10 stands up towards the inside.

Figure 5:
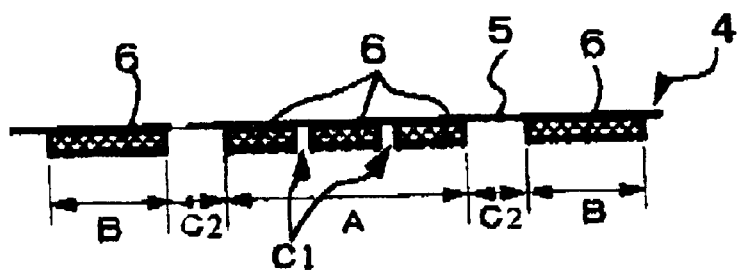
FIG. 5 is a schematic cross-section view of an embodiment of an absorbent unit to be used in an absorbent incontinence pad shown in FIG. 4.

The absorbent unit 4, of FIG. 4 is depicted in FIG. 5. The absorbent unit 4 has a nearly rectangular non-woven fabric substrate 5. A first absorbent zone A is adjacent to the center region of the non-woven fabric substrate 5. The first absorbent zone A is comprised of three parallel highly absorbent layer strands 6 spaced by narrow air permeable zones C1. A pair of second absorbent zones B comprised of highly absorbent layers 6 are situated on both sides of the first absorbent zones A with the highly absorbent layers 6 placed in parallel with those of the first absorbent zone A. Wider air permeable zones C2 separate the second absorbent zones B from the first absorbent zones A.

The ratio of the width of a first absorbent zone A (Aw) to the width of a second absorbent zone B (Bw), (Aw:Bw), is preferably in the range of 1:0.3 to 2 and more preferably in the range of 1:0.7 to 1.0. Also, it is preferred that the air permeable zone C2 separating the first and second absorbent zones A and B occupies 10% or more of the total area of the absorbent unit and more preferably 15% to 50%.

By placing the first absorbent zone A in the center and the second absorbent zones B on both sides of the first absorbent zone A, it is easier to impart different absorbency properties in each zone and easier to tailor products having properties that meet various application requirements. At the same time, this embodiment provides for a structures that can easily be intentionally changed in form.

Furthermore, under conditions in which an absorbent incontinence pad will be wetted after an act of incontinence, the air permeable zones C1 and C2 function to impart excellent air permeability to the absorbent incontinence pad, preventing the pad from becoming hot, stuffy, or otherwise uncomfortable.

Referring back to FIG. 4, a heat seal 9 links the absorbent unit 4 to other elements, such as the dispersion sheet 7, the tissue 8, the top sheet 1, and the back sheet 2, and integrates all of these elements. Thus integrated, the absorbent unit 4 is secured in place and the absorbent unit 4 and the absorbent incontinence pad maintain their initial shape. Also, this heat seal 9 provides a passage through which liquid moves up and down and specifically functions as a short passage for the liquid moving from the top sheet down to the piece of tissue layer 8.

Figure 6:
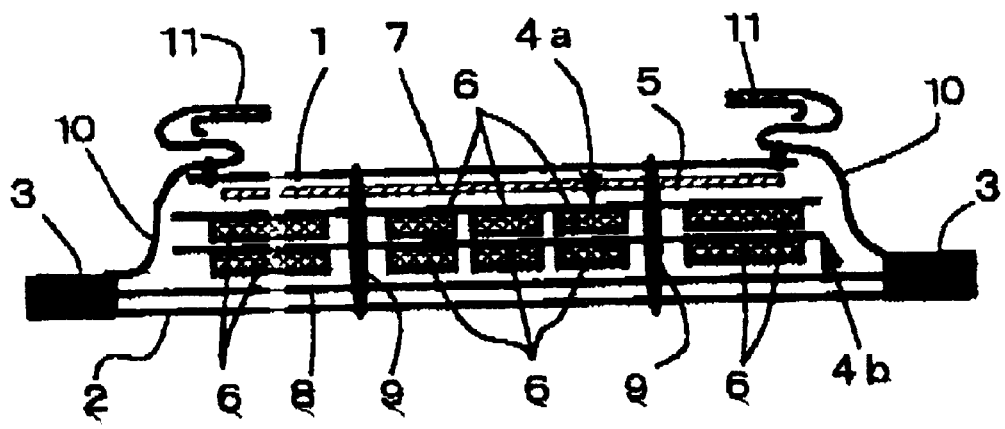
FIG. 6 is a schematic cross-sectional view showing an absorbent incontinence pad in the form of a third embodiment of the present invention.

FIG. 6 shows a third embodiment of the present invention in which an absorbent incontinence pad is designed, according to the present invention, to absorb more liquid for longer a period of time. In this example, there are two absorbent units 4a and 4b (a dual structure absorbent unit), each having a structure similar to that of the absorbent incontinence pad shown in FIG. 4. The other elements in FIG. 6 are similar to, and use the same reference numbers as those of the absorbent incontinence pad shown in FIG. 4, and so no explanation of those elements is necessary here.

The embodiment depicted in FIG. 6 exhibits an extremely high absorbent capacity while maintaining outstanding air permeability. In this embodiment, the dispersion sheet 7 is located between the top sheet 1 and the upper non-woven fabric substrate 5, however, the top sheet 1 may be located between the non-woven fabric substrate 5 and the dispersion sheet 7.

In another embodiment of the present invention, shown in FIG. 7, two absorbent sheets 4a and 4b are connected together by heat seals 9 at two points, and are wrapped with a back sheet 2 having elastic bands 12 and 13 along the periphery thereof in such manner that the upper surface of the uppermost absorbent sheet 4a is left uncovered. An acquisition layer 7' is disposed on the uppermost absorbent sheet 4a, covering all or part of the surface left uncovered by the back sheet 2.

The embodiment shown in FIG. 7 may be modified as shown in FIG. 8. In FIG. 8, the pair of absorbent sheets 4a and 4b are entirely enveloped by a dispersion sheet 14. As in the previous example, a back sheet 2 having elastic bands 12 and 13 along its periphery is wrapped around the absorbent sheets 4a and 4b and the dispersion sheet 14, leaving a portion of the dispersion sheet 14 exposed. An acquisition layer 7' is located on all or part of the exposed portion of the dispersion sheet 14.

In the embodiments shown in FIGS. 7 and 8, the top sheet is omitted, and only an acquisition layer 7' is made adjacent to the uppermost absorbent unit 4a, either directly or via the dispersion sheet 14. One advantage of such arrangements is that the absorbent unit or units can swell and expand without any restraint caused by the top sheet on the upper surface thereof. In such embodiments, it is preferred that the acquisition layer be made from a bulky sheet having a weight of 30 g/m$^2$ or more, or a compressed sheet of such a material. Examples of such material include a bulky perforated film having an embossed thickness of 1184$\mu$ (such as that manufactured and sold by Tredegar under the trademark of "X-27373"), or a compressed sheet of cellulose sponge having a weight of approximately 100 g/m$^2$, or a bulky non-woven fabric made of hollow bicomponent fiber and having a density of about 50 g/m$^2$.

Figure 9:
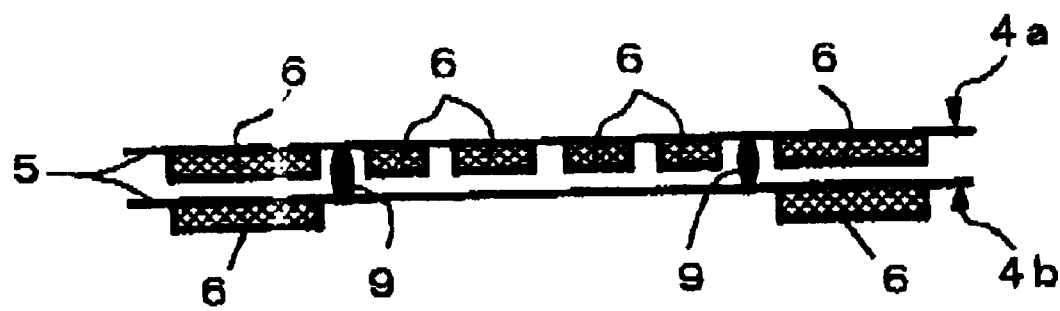
FIG. 9 is a longitudinal cross-sectional view showing the structure of an embodiment of an absorbent unit to be applied to the present invention.

Another embodiment of an absorbent unit for use in an absorbent incontinence pad made according to the present invention is shown in FIG. 9. The embodiment of the absorbent unit in FIG. 5 is comprised of two nearly rectangular non-woven fabric substrates 5. The uppermost absorbent sheet 4a is comprised of the upper non-woven fabric substrate 5, to which an inboard set of four highly absorbent layers 6 are attached, extending in parallel and centered on the substrate. In addition, the uppermost absorbent sheet has an outboard pair of highly absorbent layers 6, one of which is located on either side of the inboard strands. The lower absorbent sheet 4b is comprised of a non-woven fabric substrate, attached to which are a pair of outboard highly absorbent layers located in a position corresponding to the positions of the outboard strands attached to the uppermost absorbent sheet 4a. The absorbent sheets 4a and 4b are linked to each other, an possibly to other elements of the article, by means of heat seals 9.

The embodiment of the absorbent unit depicted in FIG. 9 has a much higher absorbing capacity on either side than in the center. It may also be easily bent or deformed in the portion where the heat seal 9 is located. Such an absorbent unit is able to change shape and conform to the user's body, and is particularly useful in applications in which the user needs to be free from leakage from the sides.

Figure 10:
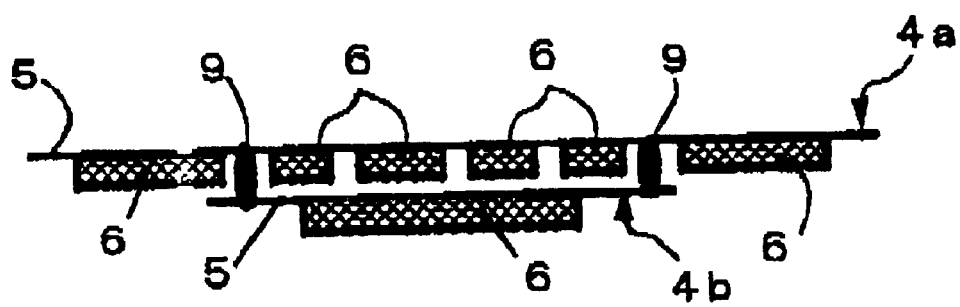
FIG. 10 is a longitudinal cross-sectional view showing the structure of another embodiment of an absorbent unit to be applied to the present invention.

In another embodiment of an absorbent unit depicted in FIG. 10, a first absorbent sheet 4a has a structure similar to the one shown in FIG. 9. The second absorbent sheet 4b has a single highly absorbent layer strand 6 only in the second absorbent sheet's 4b center portion. The first and second absorbent sheets 4a and 4b are linked to each other by means of a heat seal 9. In this embodiment, the pad exhibits a very high absorbing capacity in the center portion and has a bulky area, also in the center portion, which swells as the absorbent unit absorbs liquid.

Figure 11A:
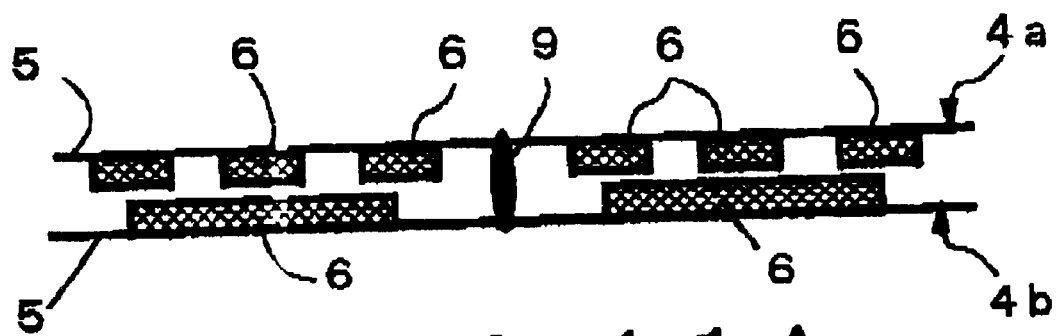
FIG. 11A is a longitudinal cross-sectional view showing the structure of another embodiment of an absorbent unit to be applied to the present invention.
Figure 11B:
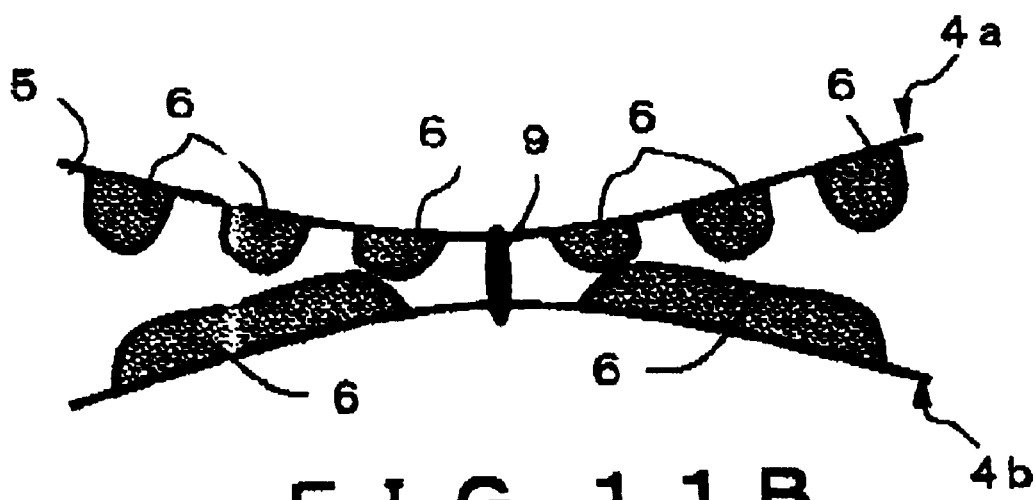
FIG. 11B is a longitudinal cross-sectional view showing the structure of still another embodiment of an absorbent unit to be applied to the present invention.
Figure 12:
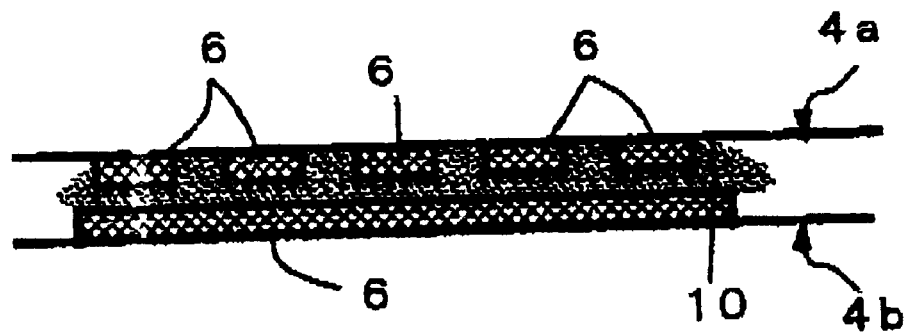
FIG. 12 is a longitudinal cross-sectional view showing the structure of yet another embodiment of an absorbent unit to be applied to the present invention.

In yet another embodiment of an absorbent unit, shown in FIG. 11a, the absorbent unit is comprised of a first absorbent sheet 4a and a second absorbent sheet 4b bonded to each other in the respective center portions of each sheet by means of a heat seal 9. An absorbent unit of this embodiment becomes swollen on either side of the centerline after it has absorbed liquid, as shown in FIG. 11B.

In an embodiment in which a heat seal is used, it is a general practice to have a thermally fusible fibrous material in coexistence inside the non-woven fabric substrate 5. However, in an embodiment in which the non-woven fabric substrate 5 has no thermally fusible material, an adhesive such as a hot melt adhesive may be used to bond the non-woven fabric substrate 5.

FIG. 10 shows an embodiment of an absorbent unit wherein a first absorbent sheet 4a and a second absorbent sheet 4b are bonded to each other by means of a hot melt adhesive layer 10 interposed between the sheets. By such bonding, liquid may much more easily move in the upward and downward directions.

Dual structure absorbent units, such as those depicted in FIGS. 6 to 12, can be selected and configured to optimize the absorbing capacities and shape conforming abilities of the absorbent pad to meet the requirements of many different applications and user. Although the foregoing explanation has been focused on dual structure absorbent units comprised of two absorbent sheets, it is possible to have a triple structure, with three sheets, or even a quadruple structure of four absorbent sheets in order to obtain higher absorbency capabilities.

Although the embodiments of the present invention that have been discussed have indicated that the non-woven fabric substrate is located on the top with the highly absorbent layers on the bottom, it should be understood that the positional relation between the two may be reversed, such that the substrate is below the strands. Also, in embodiments in which a dual structure absorbent unit is used, the positional relation and orientation of either or both of the two absorbent sheets may be reversed and the highly absorbent layers may be placed such that they face each other, as in FIG. 12. Furthermore, although in the many embodiments discussed herein the band-like highly absorbent layers have been described as extending in parallel with the longitudinal direction of an absorbent incontinence pad, they can also be designed to extend orthogonally to longitudinal direction of the absorbent incontinence pad. In an embodiment using a dual structure absorbent unit, one set of strands may be parallel with and the other orthogonal to the longitudinal direction of the absorbent incontinence pad.

Although the foregoing explanations have focused on embodiments of absorbent pads for light incontinence, it should be understood that the present invention may be applied to uses ranging from extremely light incontinence pads to baby and adult diapers, by simply changing the dimensions and proportions explained in the embodiments herein.

What is claimed is:

1. An absorbent incontinence pad comprising:
   an absorbent unit (4) comprising a non-woven fabric substrate (5), an absorbent zone consisting of a plurality of highly absorbent layer elements (6) extending in bands on a surface of the non-woven fabric substrate (5), and an air permeable zone abutting the non-woven fabric substrate (5) formed in one or more areas where the highly absorbent layers (6) are not formed;
   a back sheet (2) wrapping the absorbent unit (4) leaving part of a surface of the absorbent unit (4) uncovered; and
   an acquisition layer (7) disposed on the surface of the absorbent unit (4) covering at least part of the uncovered surface thereof.

2. The absorbent incontinence pad of claim 1, wherein the absorbent unit (4) is wrapped with a dispersion layer (14), and wherein the acquisition layer is disposed on the dispersion layer and covers at least part of the uncovered surface of the absorbent unit (4).

3. The absorbent incontinence pad of claim 1, wherein the absorbent unit (4) is comprised of a plurality of absorbent sheets (4a, 4b) folded on each other.

4. The absorbent incontinence pad of claim 3, wherein the absorbent unit (4) is composed of a first absorbent sheet (4a) and a second absorbent sheet (4b) as folded onto each other, the first absorbent sheet (4a) having highly absorbent layers (6) in a position corresponding to a first absorbent zone and a second absorbent zone and the second absorbent sheet having a highly absorbent layer (6) in a position corresponding to only the second absorbent zone.

5. The absorbent incontinence pad of claim 3, wherein the absorbent unit (4) is composed of a first absorbent sheet (4a) and a second absorbent sheet (4b) as folded on each other, the first absorbent sheet (4a) having highly absorbent layers (6) in positions corresponding to a first absorbent zone and a second absorbent zone, respectively and the second absorbent sheet (4b) having a highly absorbent layer (6) in a position corresponding to only the first absorbent zone.

6. The absorbent incontinence pad of claim 4 or 5, wherein a ratio (Aw:Bw) of a width of the first absorbent zone (Aw) to a width of the second absorbent zone (Bw) is in a range of 1:0.3 to 2.

7. The absorbent incontinence pad of claim 3, wherein the plurality of absorbent sheets (4a, 4b) are bonded to each other.

8. The absorbent incontinence pad of claim 3, wherein the plurality of absorbent sheets (4a, 4b) are entirely bonded to each other by means of a hot melt (9) resin interposed between the adjacent absorbent sheets.

9. The absorbent incontinence pad of claim 1, wherein the highly absorbent layer (6) is comprised mainly of a super absorbent polymer.

10. The absorbent incontinence pad of claim 9, wherein the highly absorbent layer (6) contains 60% or more by weight of a super absorbent polymer.

11. The absorbent incontinence pad of claim 9, wherein the highly absorbent layer (6) is comprised of a mixture of a super absorbent polymer and microfibrillated fibrils.

12. The absorbent incontinence pad of claim 9, wherein the highly absorbent layer (6) is divided into a plurality of rows extending in parallel with each other.

13. The absorbent incontinence pad of claim 1, wherein the non-woven fabric substrate (5) is bonded with the back sheet (2) in the air permeable zone.

14. The absorbent incontinence pad of claim 1, wherein all of the constituting elements of the absorbent incontinence pad are composed of biodegradable materials.

15. The absorbent incontinence pad of claim 1, wherein all of the constituting elements of the absorbent incontinence pad are composed of water decomposable materials.

16. An absorbent incontinence pad comprised of a topsheet (1) comprised of a liquid pervious air permeable sheeting material, a liquid impervious air permeable back sheet (2) and an absorbent unit (4) interposed between the back sheet (2) and the top sheet (1), the absorbent unit (4) comprising:

a non-woven fabric substrate (5), an absorbent zone comprised of a plurality of highly absorbent layers (6) extending in bands on a surface of the non-woven fabric substrate (5), and an air permeable zone abutting the non-woven fabric substrate (5) formed in one or more areas where the highly absorbent layers (6) are not formed.

17. The absorbent incontinence pad of claim 16, wherein the back sheet (2) and the top sheet (1) are bonded to each other on their perimeter portions with the absorbent unit (4) located between the top sheet (1) and back sheet (2).

18. The absorbent incontinence pad of claim 16, wherein the non-woven fabric substrate (5) is bonded with the top sheet (1) in the air permeable zone.

19. The absorbent incontinence pad of claim 16, wherein the non-woven fabric substrate (5) is bonded with the back sheet (2) and the top sheet (1) in the air permeable zone.

20. The absorbent incontinence pad of claim 16, wherein the absorbent unit (4) is comprised of a plurality of absorbent sheets (4a, 4b) folded on each other.

21. The absorbent incontinence pad of claim 20, wherein the absorbent unit (4) is composed of a first absorbent sheet (4a) and a second absorbent sheet (4b) as folded on each other, the first absorbent sheet (4a) having highly absorbent layers (6) in a position corresponding to a first absorbent zone and a second absorbent zone and the second absorbent sheet having a highly absorbent layer (6) in a position corresponding to only the second absorbent zone.

22. The absorbent incontinence pad of claim 20, wherein the absorbent unit (4) is composed of a first absorbent sheet (4a) and a second absorbent sheet (4b) as folded on each other, the first absorbent sheet (4a) having highly absorbent layers (6) in positions corresponding to a first absorbent zone and a second absorbent zone, respectively and the second absorbent sheet (4b) having a highly absorbent layer (6) in a position corresponding to only the first absorbent zone.

23. The absorbent incontinence pad of claim 21, wherein a ratio (Aw:Bw) of a width of the first absorbent zone (Aw) to a width of the second absorbent zone (Bw) is in a range of 1:0.3 to 2.

24. The absorbent incontinence pad of claim 20, wherein the plurality of absorbent sheets (4a, 4b) are bonded to each other.

25. The absorbent incontinence pad of claim 20, wherein the plurality of absorbent sheets (4a, 4b) are entirely bonded to each other by means of a hot melt (9) resin interposed between the adjacent absorbent sheets.

26. The absorbent incontinence pad of claim 16, wherein the highly absorbent layer (6) is comprised mainly of a super absorbent polymer.

27. The absorbent incontinence pad of claim 26, wherein the highly absorbent layer (6) contains 60% or more by weight of a super absorbent polymer.

28. The absorbent incontinence pad of claim 26, wherein the highly absorbent layer (6) is comprised of a mixture of a super absorbent polymer and microfibrillated fibrils.

29. The absorbent incontinence pad of claim 26, wherein the highly absorbent layer (6) is divided into a plurality of rows extending in parallel with each other.

30. The absorbent incontinence pad of claim 16, wherein the non-woven fabric substrate (5) is bonded with the back sheet (2) in the air permeable zone.

31. The absorbent incontinence pad of claim 16, wherein all of the constituting elements of the absorbent incontinence pad are composed of biodegradable materials.

32. The absorbent incontinence pad of claim 16, wherein all of the constituting elements of the absorbent incontinence pad are composed of water decomposable materials.

33. The absorbent incontinence pad of claim 5, wherein a ratio (Aw:Bw) of a width of the first absorbent zone (Aw) to a width of the second absorbent zone (Bw) is in a range of 1:0.3 to 2.

34. The absorbent incontinence pad of claim 17, wherein the non-woven fabric substrate (5) is bonded with the top sheet (1) in the air permeable zone.

35. The absorbent incontinence pad of claim 17, wherein the non-woven fabric substrate (5) is bonded with the back sheet (2) and the top sheet (1) in the air permeable zone.

36. The absorbent incontinence pad of claim 22, wherein a ratio (Aw:Bw) of a width of the first absorbent zone (Aw) to a width of the second absorbent zone (Bw) is in a range of 1:0.3 to 2.

* * * * *